United States Patent [19]

Bellis et al.

[11] Patent Number: 5,684,191
[45] Date of Patent: Nov. 4, 1997

[54] PROCESS FOR THE COMBINED SYNTHESIS OF BETAINE AND CHOLINE CHLORIDE

[75] Inventors: Harold Edward Bellis, Wilmington, Del.; Thomas Robert Jemison, Nixa, Mo.; Owen B. Mathre, Wilmington, Del.

[73] Assignee: DuCoa, L.P., Highland, Ill.

[21] Appl. No.: 741,795

[22] Filed: Oct. 31, 1996

[51] Int. Cl.$^6$ ............................................. C07C 229/00
[52] U.S. Cl. ................................................. 562/575
[58] Field of Search ...................................... 562/575

[56] References Cited

U.S. PATENT DOCUMENTS

| | | | |
|---|---|---|---|
| 5,075,498 | 12/1991 | Perine | 562/575 |
| 5,081,293 | 1/1992 | Borland | 562/575 |
| 5,105,008 | 4/1992 | Sauer | 562/575 |
| 5,120,873 | 6/1992 | Perine | 562/575 |
| 5,292,942 | 3/1994 | Aigner | 562/575 |

*Primary Examiner*—Michael L. Shippen

[57] ABSTRACT

A process for the combined synthesis of betaine and choline chloride from monochloroacetic acid, trimethylamine and ethylene oxide by first reacting trimethylamine with monochloroacetic acid, and then reacting ethylene oxide with the reaction product from the previous step.

8 Claims, No Drawings

PROCESS FOR THE COMBINED SYNTHESIS OF BETAINE AND CHOLINE CHLORIDE

FIELD OF INVENTION

The invention is directed to a process for the combined synthesis of aqueous solutions of betaine and choline chloride. In particular, the invention is directed to such process in which the betaine and choline chloride solutions are especially adapted for use in animal feed applications.

BACKGROUND OF THE INVENTION

Betaine is a well-known product which has been used widely in a number of applications for many years. Until recently, betaine was used mainly in cosmetics, fish food and as a supplement in food for humans. Recently, new uses of betaine have been investigated, especially incorporation of betaine into feed for swine and poultry. Consistent with a current trend to decrease the amount of human fat intake, the primary use in swine feed is centered around the effectiveness of betaine to decrease the amount of backfat on finishing pigs. In addition there is considerable interest in the effectiveness of betaine as a cellular osmotic regulator. In this application, betaine improves the functionality and integrity of intestinal cell walls by which nutrient absorption and animal health are improved and dehydration is limited.

Heretofore, most of the betaine has been derived from natural sources such as beet molasses. Natural sources of betaine are, however, limited and are variable. Frequently, climate variations seriously reduce the production of betaine from natural sources and may be insufficient to meet the prospective demands for the product. Several synthetic routes to the production of betaine have been proposed. For example, Brazilian patent PI 9301144-0 A is directed to making an animal feed supplement comprising betaine and wheat bran. The betaine is produced by reaction of sodium monochloroacetate, trimethyl ammonium chloride and sodium hydroxide in aqueous solution. The pH of the reaction mixture is adjusted with HCl, after which it is concentrated to precipitate NaCl, which is removed from the reaction mixture by filtration. This process is technologically feasible, but the product is isolated as a crystalline solid along with substantial quantities of trimethylaminehydrochloride and unreacted sodium monochloroacetate.

Choline has long been recognized as an essential nutrient in both human and animal diets and has been available commercially for more than forty years. The primary functions of choline are (1) nerve transmission; (2) as a component in cell membranes; (3) as a lipotropic (fat metabolism) agent; and (4) as a methyl group donor in the production of DNA and other body compounds.

The worldwide demand for choline has been growing steadily as more information about its essential nature has been discovered. Though most current use of choline is in animal diets, it is nevertheless used extensively in human diets as well. The need for choline tends to be greatest in the diets of growing animals. Since the availability of choline from natural ingredients and body synthesis is not sufficient, choline must be supplemented in the diet. Synthetic choline is preferred for this purpose since it has been readily available at reasonable costs.

Choline and betaine are similar in structure. In fact, for some functions of choline, it is oxidized to betaine (methyl donation) and betaine donates the methyl group in the body. This is not an extremely efficient mechanism, however, and supplemental betaine appears to be a more efficient method for supplying betaine for methyl donation.

Betaine also has a function in the body which is independent of choline. This function appears to be oriented around the osmotic regulation of cells, especially intestinal cells. Most production animals (poultry, swine, etc.) are under considerable stress (rapid growth, high energy diets etc.) and adding supplemental betaine helps the overall health of the animal.

Not only do choline and betaine have similar structures, they are closely associated in the cell itself. For instance, choline is important for cell wall integrity and betaine, located in the cytoplasm of the cell, is important for osmotic integrity of the cell.

The close proximity of each compound within the body and cells makes it advantageous to supply both compounds simultaneously to the animal. This ensures that both products are consumed by the animal at adequate amounts and at appropriate times.

Previously, users of both betaine and choline chloride have produced these materials as separate, purified solid products, which require the use of special mixing equipment to place them in form for use in animal feed. Therefore, most animal producers would prefer to have betaine and choline chloride provided in combination for several reasons: (1) it assures that they will be administered together and lessens the chance that either might be omitted; (2) it assures that the proportions of each will be correct; (3) it assures that optimal utilization by the body will be obtained; and (4) it eliminates the cost for separate equipment to handle each product.

For these reasons, there exists a substantial need for a process by which betaine and choline chloride can be synthesized economically with high purity to form a single aqueous liquid composition containing approximately equal amounts of both betaine and choline chloride.

SUMMARY OF THE INVENTION

The invention is therefore directed to a highly efficient process for the combined synthesis of betaine and choline chloride, which is carried out in such manner that there is no need for the isolation and purification of solid products. The process consists of five steps which are carried out in such manner that high yields of aqueous solutions of betaine and choline chloride are obtained with a minimal amount of by-products, by controlling the reaction conditions and the proportions of reactants. Furthermore, what few by-products are produced by this process are readily removed in a single stripping step.

In particular, the process of the invention is directed to the combined synthesis of betaine and choline chloride comprising the following sequence of steps carried out in a closed vessel with continuous mixing:

(1) increasing the pH of an aqueous solution of monochloroacetic acid to 5–6 by adding thereto a stoichiometric excess of liquid trimethylamine with the concomitant formation of trimethylammoniumchloroacetate;

(2) maintaining the reaction solution from step (1) at pH 7.5–10, as necessary, by addition of a molar excess of liquid trimethylamine, to effect the formation of betaine and trimethyl ammonium hydrochloride until substantially all of the monochloroacetic acid has been reacted, leaving a residual amount of trimethylammoniumchloroacetate in the reaction solution;

(3) adding liquid ethylene oxide to the alkaline reaction mixture from step (2) to effect formation of (a) choline chloride by reaction of the ethylene oxide with the trimethyl ammonium hydrochloride, (b) choline hydroxide by reaction of the ethylene oxide with excess trimethylamine, (c) a minor amount of choline chloride by reaction of the choline hydroxide with the trimethyl ammonium hydrochloride until all of the trimethyl ammonium hydrochloride has been reacted, (d) additional betaine by reaction of excess trimethylamine with the residual amount of trimethylammoniumchloroacetate in the reaction solution;

(4) as necessary, adding either trimethylamine or NaOH to the reaction solution from step (3) to raise the pH to 10–12 and stripping any excess trimethylamine from the solution, while converting any residual amounts of monochloroacetic acid to glycolic acid; and (5) Adjusting the pH of the stripped product from step (4) to pH 6–8 by addition of hydrochloric acid.

DETAILED DESCRIPTION OF THE INVENTION

Only three primary reactants are used in the process, namely trimethylamine, monochloroacetic acid and ethylene oxide. Sodium hydroxide and hydrochloride acid are used, as needed, only for pH adjustment. Overall, the process is carried out in such manner as to produce concentrated aqueous solutions.

Aqueous Medium

The amount of water present in the reaction steps of the invention is not critical from the standpoint of the synthesis steps involved. However, the amount of water is important from the standpoint that enough must be present so that the products and by-products produced in each step of the process remain dissolved at all process temperatures and foreseeable storage temperatures. For this reason, it is preferred that the amount of water introduced with the monochloroacetic acid be sufficient that the final stripped betaine/choline chloride solution contains at least 20% by weight water. At least 25% wt. water is further preferred. Higher amounts of water can be used, but have no apparent advantage.

Reactants

The principal reactants in the process of the invention are monochloroacetic acid, trimethylamine and ethylene oxide. Overall, the process is intended to synthesize concentrated solutions of approximately equal molar amounts of betaine and choline chloride (wt. ratio 33/37 betaine/choline chloride). Thus, approximately two moles of trimethylamine are used per mole of monochloroacetic acid and ethylene oxide.

To avoid the necessity of adding a supplemental base to adjust pH of the reaction solution at the end of step (3), it is preferred to use a small molar excess of the trimethylamine. Even though the process of the invention proceeds at higher pH levels, it is nevertheless preferred not to exceed a molar ratio of 2.4:1 in order to avoid the formation of colored by-products. It is further preferred to carry out the process at a trimethylamine/monochloroacetic acid-ethylene oxide molar ratio below 2.4:1 in order to lower the choline chloride/betaine ratio. Overall, the process is best carried out at molar ratios of 2.05:1–2.1:1. Within this range, the amount of side reactions and unwanted by-products are minimized and process efficiency is highest.

An important factor affecting the efficiency of the process is that the amount of oxygen must be kept very low to prevent side reactions of the trimethylamine. Therefore, it is preferred that any oxygen contained in the aqueous monochloroacetic acid solution and in the head space of the reactor be removed. This is easily done by means of purging the acid solution and the reactor with gaseous nitrogen before introduction of trimethylamine.

Process Operating Variables

To attain higher efficiency in conducting the process, it is preferred that both the pH and temperature be controlled in each step by addition of trimethylamine. By this means, unwanted side reaction are reduced and reaction rates are raised. It should be noted that the process must be carried out in glass-surfaced (glass or glass-lined) reactors in order to prevent iron contamination.

Step (1) is carried out at pH 5–6 and a temperature of 30–50 C. in order to prevent hydrolysis of the monochloroacetic acid. The progress of step (1) can be monitored by measuring chloride formation in the reaction solution. At the conclusion of step (1), the level of free chloride is normally less than 0.1% wt.

In step (2), it is has been found that higher temperatures reduce the solubility of trimethylamine, increase reactor pressure and slow down reactions of trimethylamine with the monochloroacetic acid and the ethylene oxide. Higher temperatures also cause the formation of unwanted by-products, such as glycolic acid. In view of these factors, it is preferred that the temperature of the reaction solutions in step (2) be maintained at a level of 40–70 C., and preferably 45–60 C. This temperature range is sufficiently low to give good reaction rates, yet high enough to avoid the odor of trimethylamine in the reaction solution.

At the end of step two, during which the principal amount of betaine is formed, it is important that substantially all of the monochloroacetic acid be reacted before proceeding to the next reaction step. The level of unreacted acid should not exceed 0.1% wt., and preferably not more than 0.05% wt., basis acid weight.

In step (3), a stoichiometric excess of ethylene oxide is added to the reaction solution from step (2) until all the trimethyl ammonium hydrochloride and trimethylamine are converted. This point in the process is indicated by a sharp rise to 10 of the pH of the reaction solution.

At the end of step (3), in which the choline chloride is formed, it is essential in step (4) to remove any unreacted trimethylamine in order to avoid odor therefrom and to meet product specifications. This can be done easily by stripping, for example, with gaseous nitrogen and/or vacuum. To facilitate removal of the trimethylamine, it is preferred to have the pH at a level of about 10. If the pH of the reaction is below 10, it can be raised most easily by the addition of a small amount of aqueous base. Only a small amount of such base will be required since the pH of the reaction solution at the end of step (3) is already close to 10.

Soluble base materials for this use include organic bases, such as trimethylamine and choline hydroxide, and aqueous solutions of the hydroxides of alkali metals and alkaline earth metals. Basic compounds of other metals, both organic and inorganic, are operable for this limited purpose; however, their use is not preferred since it is desirable to minimize the addition of metals to the product of the invention. Among the inorganic bases, aqueous sodium hydroxide is preferred for economic reasons.

It has been found that the reactions involved in this process are mass transfer limiting. Therefore, it is essential that the process be carried out with thorough mixing. Highly turbulent mixers may not be required. For example, propeller mixers and turbine mixers and even recirculating pumps are suitable for use in practicing the invention. However, thorough mixing must be obtained throughout all steps of the process to lessen side reactions and reduce cycle times.

EXAMPLES

An aqueous solution of betaine and choline chloride was prepared in a 140 gallon stirred reactor using the following procedure:

The reactor and feed lines were thoroughly cleaned and the reactor vessel was purged with N2 gas and then charged with 443 pounds of water and 272 pounds of flake monochloroacetic acid (MCAA). The pH of the aqueous MCAA solution was 1.9. When the MCAA charge was completed, the MCAA solution was treated with 340 pounds of liquid trimethylamine (TMA) in the bottom of the vessel over a period of almost 6 hours, by which the pH was raised to 8.5. At the beginning of the TMA charge, the temperature of the MCAA solution was 19 C. During the addition of TMA, the temperature rose to 52 C. and the reactor contents were cooled to 40 C. Reactor pressure rose to as high as 42 psig during TMA addition, but fell to 30 psig at the end of charging the TMA. The pH of the reactor contents was 8.5. Upon completion of TMA addition and cooling of the reactor contents, 127 lbs. of liquid ethylene oxide (EO) was added to the reactor over a period of about 2.5 hours, during which the reactor pressure rose to about 43 psig at a temperature of 42 C. and pH 6.8. Upon completion of EO addition, the liquid reactor contents, having a pH of 10.5, were stripped under vacuum with nitrogen gas to remove any unreacted TMA and EO. During stripping, the temperature of the reaction solution rose to 80 C. The pH of the reaction solution stayed at 6.8.

Upon analysis, the reaction product contained 29.2% wt. betaine and 36.2% choline chloride, the remainder being water. This is equivalent to a 65%. molar concentration.

Example 2

A clean 2,000 gallon reactor was purged with nitrogen gas and charged with 5095 lbs. of flake MCAA and 2810 lbs. of water. The temperature of the completed charge was 26 C. and the pH was 0.2. Upon completion of charging the MCAA, 5155 lbs. of liquid TMA was added through a circulating pump into the bottom of the reactor over the course of about 7.75 hours. At the end of that time, the pH rose to 6.2, at a temperature of 39 C. and pressure of 27 psig. After letting the reaction product from the previous addition stand for about 2 hours, 1735 lbs. of EO was added to the reactor over a period of about 5 hours, during which the pH of the reaction solution rose to 8.0 at a pressure of 34.4 psig and temperature of 48 C. About 45 minutes later, 830 lbs. of NaOH was added to the reactor, during which the pH rose to 11.6 and a temperature of 50 C. At that time, the reaction solution was stripped under vacuum with nitrogen gas for about 5 hours to remove unreacted EO and TMA. Weight of the reaction solution after stripping was 15,005 lbs. with a pH of 7.3. The stripped material contained 33.7% wt. betaine, including a small amount of glycolic acid, and 44.7% wt. choline chloride, which is a 78% wt. concentrated solution of equi-molar amounts of betaine and choline chloride. The stripped solution contained only 7 ppm by weight TMA as trimethylaminehydrochloride.

Example 3

A 6,000 gallon, glass-lined, stirred reactor having interior cooling coils, was cleaned and purged with nitrogen gas. The reactor was then charged with 14,900 lbs. of 80% aqueous MCAA (12,054 lbs. MCAA, 2846 lbs. water) and 8,245 lbs. of water. This charge had pH 1.9 and a temperature of 24 C. To this aqueous solution of MCAA, 15,020 lbs. of TMA were added to the reactor continuously through an inlet in the bottom of the reactor. The solution was held at 40–45 C. for one hour, after which 5,856 lbs. of EO were added. The resultant reaction solution had a pH of 9.5 at a temperature of 53 C. and 20 psig pressure. This solution was then stripped under vacuum with nitrogen gas for four hours, after which the solution contained less than 10 ppm MCAA, about 7 ppm trimethylamine and less than 0.05 ppm ethylene oxide. The stripped solution was treated with 277 lbs. of 32% wt. aqueous HCl solution, which reduced the pH to 6.5. The product contained 35% wt. betaine and 42.3% wt. choline chloride. Furthermore, the product was clear and water-white and exhibited no crystallization or settling of solids upon storage at minus 11 C. Total cycle time was 18 hours.

What is claimed is:

1. A process for the combined synthesis of betaine and choline chloride comprising the following sequence of steps carried out in a closed vessel with continuous mixing:
   (1) increasing the pH of an aqueous solution of monochloroacetic acid to 5–6 by adding thereto liquid trimethylamine with the concomitant formation of trimethylammoniumchloroacetate;
   (2) maintaining the reaction solution from step (1) at pH 7.5–10, as necessary, by addition of a molar excess of liquid trimethylamine, to effect the formation of betaine and trimethyl ammonium hydrochloride until substantially all of the monochloroacetic acid has been reacted, leaving a residual amount of trimethylammoniumchloroacetate in the reaction solution;
   (3) adding liquid ethylene oxide to the reaction mixture from step (2) to effect formation of (a) choline chloride by reaction of the ethylene oxide with the trimethyl ammonium hydrochloride, (b) choline hydroxide by reaction of the ethylene oxide with excess trimethylamine, (c) a minor amount of choline chloride by reaction of choline hydroxide with the trimethyl ammonium hydrochloride until all of the trimethyl ammonium hydrochloride has been reacted and (d) additional betaine by reaction of excess trimethylamine with the residual amount of trimethylammoniumchloroacetate in the reaction solution;
   (4) as necessary, adding base to the reaction solution from step (3) to raise the pH to 10–12 and stripping any residual trimethylamine from the solution, while converting any residual amounts of chloroacetic acid to glycolic acid; and
   (5) adjusting the pH of the stripped product from step (4) to pH 6–8 by addition of hydrochloric acid.

2. The process of claim 1 in which the mole ratio of trimethylamine to monochloroacetic acid is above 2.0:1, but no higher than 2.4:1.

3. The process of claim 2 in which the mole ratio of trimethylamine to monochloroacetic acid is 2.05:1–2.1:1.

4. The process of claim 1 in which the stripping operation in step (4) is carried out with steam, inert gas or by application of vacuum.

5. The process of claim 4 in which the stripping agent is nitrogen gas.

6. The process of claim 1 in which during step (1) the temperature is maintained at 30–50 C. and the pH is maintained at 5–6.

7. The process of claim 1 in which during step (2) the temperature is maintained at 40–70 C.

8. The process of claim 1 in which prior to step (1), the reactor vessel is purged with inert gas to remove oxygen therefrom.

* * * * *